United States Patent [19]

Salituro et al.

[11] Patent Number: 4,960,786

[45] Date of Patent: Oct. 2, 1990

[54] EXCITATORY AMINO ACID ANTAGONISTS

[75] Inventors: Francesco G. Salituro, Fairfield; Boyd L. Harrison; Bruce M. Baron, both of Cincinnati, all of Ohio

[73] Assignee: Merrell Dow Pharmaceuticals Inc., Cincinnati, Ohio

[21] Appl. No.: 342,498

[22] Filed: Apr. 24, 1989

[51] Int. Cl.$^5$ ............................................. A61K 31/40
[52] U.S. Cl. ................................................... 514/419
[58] Field of Search ........................................ 514/419

[56] References Cited

PUBLICATIONS

James E. Huettner, Science, vol. 245, pp. 1611–1613, (1988).

Indole-2-Carboxylic Acid: A Competitive Antagonists of Potentiation by Glycine at the NMDA Receptor, Science, vol. 243, pp. 1611–1613, Dec. 1988, James E. Huettner.

*Primary Examiner*—Stanley J. Friedman
*Attorney, Agent, or Firm*—J. Michael Dixon

[57] ABSTRACT

The present invention is directed to the discovery of a new use for a group of known 2-carboxylic indole derivatives. The compounds are excitatory amino acid antagonists.

47 Claims, No Drawings

EXCITATORY AMINO ACID ANTAGONISTS

The present invention is directed to a new pharmaceutical use for a group of known compounds. Another aspect of the invention is directed to pharmaceutical compositions containing these compounds.

In accordance with the present invention, a new class of excitatory amino acid antagonists have been discovered. These 2-carboxylic indole derivatives can be described by the following formula:

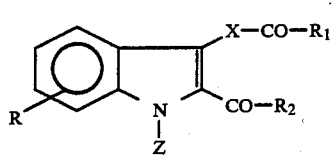

Formula I in which X is represented by a $C_{1-4}$ alkylene, Z is represented by H, $C_{1-4}$ alkyl, phenyl, substituted phenyl, or an alkylphenyl substituent in which the phenyl ring may be optionally substituted; R is represented by a substituent selected from the group consisting of hydrogen, halogen, $C_{1-4}$ alkyl, $C_{1-4}$ alkoxy, $CF_3$, $OCF_3$, OH, $NO_2$, and CN; $R_1$ and $R_2$ are each independently represented by —OH, —$OR_3$ in which $R_3$ is represented by a $C_{1-4}$ alkyl, phenyl, substituted phenyl or an alkylphenyl substituent in which the phenyl ring may be optionally substituted, —$NR_4R_5$ in which $R_4$ and $R_5$ are each independently represented by hydrogen or a $C_{1-4}$ alkyl, or —$OCH_2OR_3$ in which $R_3$ is as defined above, and the pharmaceutically acceptable basic addition salts thereof.

As used in this application:
(a) the term "halogen" refers to a fluorine, chlorine, or bromine atom;
(b) the terms "lower alkyl group and $C_{1-4}$ alkylene" refer to a branched or straight chained alkyl group containing from 1-4 carbon atoms, such as methyl, ethyl, n-propyl, isopropyl, n-butyl, isobutyl, etc.;
(c) the terms "lower alkoxy group and $C_{1-4}$ alkoxy" refer to a straight or branched alkoxy group containing from 1-4 carbon atoms, such as methoxy, ethoxy, n-propoxy, isopropoxy, n-butoxy, isobutoxy, etc.;
(d) the term "substituted phenyl ring" refers to a phenyl moiety ($C_6H_5$) which is substituted with up to 3 substituents, each substituent is independently selected from the group consisting of halogens, $C_{1-4}$ alkyl, $C_{1-4}$ alkoxy, $CF_3$, $OCF_3$, OH, CN, and $NO_2$. These substituents may be the same or different and may be located at any of the ortho, meta, or para positions.
(e) the term "alkylphenyl substituent" refers to the following structure, —$(CH_2)_m$—$C_6H_5$, in which m is an integer from 1-3. This phenyl ring may be substituted in the manner described immediately above.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

Some of the compounds of Formula I exist as optical isomers. Any reference in this application to one of the compounds represented by Formula I is meant to encompass either a specific optical isomer or a mixture of optical isomers. The specific optical isomers can be separated and recovered by techniques known in the art such as chromatography on chiral stationary phases, resolution via chiral salt formation and subsequent separation by selective crystallization, or enzymatic hydrolysis using stereoselective hydrolases as is known in the art.

The compounds depicted by Formula I contain a phenyl ring which may be optionally substituted as indicated by R. When R is represented by a substituent other than hydrogen, there can be up to 3 such substituents occurring on the indicated phenyl ring. These substituents can be located at any of the ortho, meta, or para positions. Likewise $R_1$ and $R_2$ may contain either a phenyl or an alkylphenyl substituent in which the phenyl ring may be optionally substituted. There may be up to 3 substituents occuring on these phenyl rings and these substituents may be located at any of the ortho, meta, or para positions. The specific substitutions may be any of those listed above in the definition of substituted phenyl ring.

Z may also be represented either by a substituted phenyl ring or an alkyl phenyl substituent in which the phenyl ring may be substitued. These phenyl rings may also contain up to 3 substitutents which may be located at any of the ortho, meta, or para positions. The specific substitutions may be any of those listed above in the definition of substituted phenyl ring.

X is represented by a $C_{1-4}$ alkylene. This $C_{1-4}$ alkylene may be either linear or branched. $R_1$ and $R_2$ may be represented by the same substituent or differing substitutents. Likewise $R_4$ and $R_5$ may be represented by the same substitutent or differing substitutents.

Illustrative examples of compounds encompassed by formula I include:
(a) 3-(2-Carboxyindol-3-yl)propionic acid
(b) 3-(2-Carboxy-6-methoxyindol-3-yl)propionic acid
(c) 3-(2-Carboxy-6-methoxyindol-3-yl)butyric acid
(d) 3-(2-Carboxy-6-chloroindol-3-yl)propionic acid
(e) 3-(2-Carboxy-4,6-dichloroindol-3-yl)propionic acid
(f) 3-(2-Carboxy-5-chloroindol-3-yl)propionic acid
(g) 3-(2-Carboxy-7-chloroindol-3-yl)propionic acid
(h) 3-(2-Carboxy-6-trifluoromethoxyindol-3-yl)propionic acid
(i) 3-(2-Carboxy-6-cyanoindol-3-yl)propionic acid
(j) 3-(2-Carboxy-6-hydroxyindol-3-yl)propionic acid
(k) 3-(2-Carboxy-4,6-dimethoxyindol-3-yl)propionic acid
(l) 3-(2-Carboxy-4-trifluoromethylindol-3-yl)propionic acid
(m) 3-(2-Carboxy-6-trifluoromethylindol-3-yl)propionic acid
(n) 3-(2-Carboxy-4-fluoroindol-3-yl)propionic acid
(o) 3-(2-Carboxy-6-fluoroindol-3-yl)propionic acid
(p) 3-(4-Bromo-2-carboxyindol-3-yl)propionic acid
(q) 3-(6-Bromo-2-carboxyindol-3-yl)propionic acid
(r) 3-(2-Carboxy-4-nitroindol-3-yl)propionic acid
(s) 3-(2-Carboxy-6-nitroindol-3-yl)propionic acid
(t) 3-(4-Amino-2-carboxyindol-3-yl)propionic acid
(u) 3-(6-Amino-2-carboxyindol-3-yl)propionic acid (v) 3-(2-Carboxy-4-methylindol-3-yl)propionic acid
(w) 3-(2-Carboxy-6-methylindol-3-yl)propionic acid
(x) Ethyl 3-(2-carboxyethyl-4,6-dichloroindol-3-yl) propionate
(y) Benzyl 3-(2-carboxybenzyl-4,6-dichloroindol-3-yl) propionate
(z) 3-(2-Carboxamide-4,6-dichloroindol-3-yl)propionamide
(aa) 2-(2-Carboxy-6-chloroindol-3-yl)acetic acid
(bb) 4-(2-Carboxy-6-chloroindol-3-yl)butyric acid
(cc) 5-(2-Carboxy-6-chloroindol-3-yl)pentanoic acid
(dd) 3-(2-Carboxy-4,6-dichloro-1-methylindol-3-yl)

It is preferred that the phenyl ring depicted in Formula I be mono-substituted at position 6 or di-substituted at positions 4 and 6. It is also preferred for R to be represented by a halogen atom or an alkoxy group. It is preferred for X to be represented by an ethylene group.

The 2-carboxylic indole derivatives of Formula I are known in the art. They have been utilized as intermediates in the synthesis of other classes of compounds. They have not been reported to exhibit a pharmacological utility. Methods for producing these 2-carboxylic indole derivatives are well known in the art. Examples of such methods are disclosed in:

(1) T. Nagasaka, S. Ohki, Chem. Pharm. Bull., 25 (11), 3023–3033 (1977).
(2) R. E. Bowman, T. G. Goodburn, A. A. Reynolds, *J. Chem. Soc. Perkin Trans.* 1, 1121–1123 (1972).
(3) M. D. Meyer, L. I. Kruse, *J. Org. Chem.*, 49, 3195–3199 (1984).
(4) British Pat. No. 1,004,661, Sept. 15, 1965.
(5) M. Rensen, *Bull. Soc. Chim., Belges,* 68, 258–269 (1959).
(6) W. Reid, A. Kleemann, *Justus Liebigs Ann. Chem.,* 713, 127–138 (1968).

The compounds of Formula I can be purified by methods that are known in the art. They can be purified by chromatographic techniques such as flash chromatography on a silica gel column using eluting agents known in the art such as 25% ethyl acetate in hexane. The compounds can also be purified by recrystallization techniques as is known in the art. A suitable recrystallization solvent is ethyl acetate in hexane. If desired, the compounds can be subjected to both chromatographic purification and recrystallization.

The compounds of Formula I are excitatory amino acid antagonists. They antagonize the effects which excitatory amino acids have upon the NMDA receptor complex. They preferentially bind to the strychnine-insensitive glycine binding site associated with the NMDA receptor complex. They are useful in the treatment of a number of disease states.

The compounds exhibit anti-convulsant properties and are useful in the treatment of epilepsy. They are useful in the treatment of grand mal seizures, petit mal seizures, psychomotor seizures, autonomic seizures, etc. One method of demonstrating their anti-epileptic properties is by their ability to inhibit the seizures that are caused by the administration of quinolinic acid. This test can be conducted in the following manner.

One group containing ten mice are administered 0.01–100 µg of test compound intracerebroventricularly in a volume of 5 microliters of saline. A second control group containing an equal number of mice are administered an equal volume of saline as a control. Approximately 5 minutes later, both groups are administered 7.7 micrograms of quinolinic acid intracerebroventricularly in a volume of 5 microliters of saline. The animals are observed for 15 minutes thereafter for signs of clonic seizures. The control group will have a statistically higher rate of clonic seizures than will the test group.

Another method of demonstrating the anti-epileptic properties of these compounds is by their ability to inhibit audiogenic convulsions in DBA/2 mice. This test can be conducted in the following manner. Typically one group of from 6–8 male DBA/2J audiogenic susceptible mice are administered from about 0.01 µg to about 100 µg of the test compound. The test compound is administered intracerebrally into the lateral ventricle of the brain. A second group of mice are administered an equal volume of a saline control by the same route. Five minutes later the mice are placed individually in glass jars and are exposed to a sound stimulus of 110 decibels for 30 seconds. Each mouse is observed during the sound exposure for signs of seizure activity. The control group will have a statistically higher incidence of seizures than the group which receives the test compound.

The compounds of Formula I are useful for preventing or minimizing the damage which nervous tissues contained within the CNS suffer upon exposure to either ischemic, hypoxic, or hypoglycemic conditions. Representative examples of such ischemic, hypoxic, or hypoglycemic conditions include strokes or cerebrovascular accidents, hyperinsulinemia, cardiac arrest, drownings, suffocation, and neonatal anoxic trauma. The compounds should be administered to the patient within 24 hours of the onset of the hypoxic, ischemic, or hypoglycemic condition in order for the compounds to effectively minimize the CNS damage which the patient will experience.

The compounds are also useful in the treatment of neurodegenerative diseases such as Huntington's disease, Alzheimer's disease, senile dementia, glutaric acidaemia type I, multi-infarct dementia, and neuronal damage associated with uncontrolled seizures. The administration of these compounds to a patient experiencing such a condition will serve to either prevent the patient from experiencing further neurodegeneration or it will decrease the rate at which the neurodegeneration occurs.

As is apparent to those skilled in the art, the compounds will not correct any CNS damage that has already occurred as the result of either disease, or a lack of oxygen or sugar. As used in this application, the term "treat" refers to the ability of the compounds to prevent further damage or delay the rate at which any further damage occurs.

The compounds exhibit an anxiolytic effect and are thus useful in the treatment of anxiety. The compounds also exhibit an analgesic effect and are useful in controlling pain.

In order to exhibit these therapeutic properties, the compounds need to be administered in a quantity sufficient to inhibit the effect which the excitatory amino acids have upon the NMDA receptor complex. The dosage range at which these compounds exhibit this antagonistic effect can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.1 mg/kg/day to about 50 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically an antagonistic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

As used in this application:
(a) the term "patient" refers to warm blooded animals such as, for example, guinea pigs, mice, rats, cats, rabbits, dogs, monkeys, chimpanzees, and humans;
(b) the term "treat" refers to the ability of the compounds to either relieve, alleviate, or slow the progression of the patient's disease;
(c) the term "neurodegeneration" refers to a progressive death and disappearance of a population of nerve cells occurring in a manner characteristic of a particular disease state and leading to brain damage.

The compounds of Formula I may also be admixed with any inert carrier and utilized in laboratory assays in order to determine the concentration of the compounds within the serum, urine, etc., of the patient as is known in the art.

Neurodegenerative diseases are typically associated with a loss of NMDA receptors. Thus, the compounds of Formula I may be utilized in diagnostic procedures to aid physicians with the diagnosis of neurodegenerative diseases. The compounds may be labelled with isotopic agents by techniques known in the art and utilized as imaging agents. They may then be administered to a patient in order to determine whether the patient is exhibiting a decreased number of NMDA receptors and the rate at which that loss is occurring.

What is claimed is:

1. A method for antagonizing the effects of excitatory amino acids upon the NMDA receptor complex comprising administering to a patient in need thereof, an antagonistic amount of a compound of the formula:

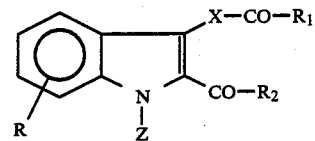

in which X is represented by a $C_{1-4}$ alkylene, Z is represented by H, $C_{1-4}$ alkyl, phenyl, substituted phenyl, or an alkylphenyl substituent in which the phenyl ring may be optionally substitued; R is represented by a substituent selected from the group consisting of hydrogen, halogen, $C_{1-4}$ alkyl, $C_{1-4}$ alkoxy, $CF_3$, $OCF_3$, $OH$, $NO_2$, and $CN$; $R_1$ and $R_2$ are each independently represented by —OH, —$OR_3$ in which $R_3$ is represented by a $C_{1-4}$ alkyl, phenyl, substituted phenyl or an alkylphenyl substituent in which the phenyl ring may be optionally substituted, $NR_4R_5$ in which $R_4$ and $R_5$ are each independently represented by hydrogen or a $C_{1-4}$ alkyl, or $OCH_2OR_3$ in which $R_3$ is as defined above, and a pharmaceutically acceptable basic addition salt thereof.

2. A method according to claim 1 wherein X is represented by a ethylene group.

3. A method according to claim 1 wherein $R_1$ and $R_2$ are represented by OH.

4. A method according to claim 1 in which R is represented by a monosubstitution occurring at position 6, or a disubstitution occurring at positions 4 and 6.

5. A method for the treatment of epilepsy comprising administering to a patient in need therof an anti-epileptic amount of a compound according to claim 1.

6. A method for the treatment of neurodegenerative diseases comprising administering to a patient in need thereof an effective amount of a compound according to claim 1.

7. A method for preventing ischemic/hypoxic/hypoglycemic damage to cerebral tissue comprising administering to a patient in need thereof an effective amount of a compound according to claim 1.

8. A method for the treatment of anxiety comprising administering to a patient in need thereof an anxiolytically effective amount of a compound according to claim 1.

9. A method for producing an analgesic effect comprising administering to a patient in need thereof an analgesic amount of a compound according to claim 1.

10. A method according to claim 4 wherein X is represented by ethylene.

11. A method according to claim 10 wherein said R is a 4,6-dichloro substituent.

12. A method according to claim 1 wherein said compound is 3-(2-Carboxy-6-methoxyindol-3-yl)propionic acid.

13. A method according to claim 1 wherein said compound is 3-(2-Carboxy-6-chloroindol-3-yl)propionic acid.

14. A method according to claim 1 wherein said compound is 3-(2-Carboxy-4,6-dichloroindol-3-yl)propionic acid.

15. A method according to claim 1 wherein said compound is 3-(2-Carboxy-6-trifluoromethoxyindol-3-yl)propionic acid.

16. A method according to claim 1 wherein said compound is 3-(2-Carboxy-4-trifluoromethylindol-3-yl)propionic acid.

17. A method according to claim 1 wherein said compound is 3-(2-Carboxy-6-trifluoromethylindol-3-yl)propionic acid.

18. A method according to claim 1 wherein said compound is 3-(2-Carboxy-4-fluoroindol-3-yl)propionic acid.

19. A method according to claim 1 wherein said compound is 3-(2-Carboxy-4-nitroindol-3-yl)propionic acid.

20. A method according to claim 1 wherein said compound is 3-(2-Carboxy-6-nitroindol-3-yl)propionic acid.

21. A method according to claim 1 wherein said compound is ethyl 3-(2-carboxyethyl-4,6-dichloroindol-3-yl) propionate.

22. A method according to claim 1 wherein said compound is benzyl 3-(2-carboxybenzyl-4,6-dichloroindol-3-yl) propionate.

23. A method according to claim 1 wherein said compound is 3-(2-Carboxamide-4,6-dichloroindol-3-yl)propionamide.

24. A method according to claim 1 wherein said compound is 2-(2-Carboxy-6-chloroindol-3-yl)acetic acid.

25. A method according to claim 1 wherein said compound is 4-(2-Carboxy-6-chloroindol-3-yl)butyric acid.

26. A method according to claim 1 wherein said compound is 5-(2-Carboxy-6-chloroindol-3-yl)pentanoic acid.

27. A method according to claim 1 wherein said compound is 3-(2-Carboxy-4,6-dichloro-1-methylindol-3-yl).

28. A pharmaceutical composition comprising an antagonistically effective amount of a compound of the formula:

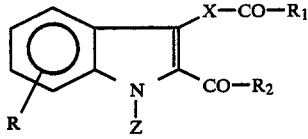

in which X is represented by a $C_{1-4}$ alkylene, Z is represented by H, $C_{1-4}$ alkyl, phenyl, substituted phenyl, or an alkylphenyl substituent in which the phenyl ring may be optionally substituted; R is represented by a substituent selected from the group consisting of hydrogen, halogen, $C_{1-4}$ alkyl, $C_{1-4}$ alkoxy, $CF_3$, $OCF_3$, OH, $NO_2$, and CN; $R_1$ and $R_2$ are each independently represented by —OH, —$OR_3$ in which $R_3$ is represented by a $C_{1-4}$ alkyl, phenyl, substituted phenyl or an alkylphenyl substituent in which the phenyl ring may be optionally substituted, —$NR_4R_5$ in which $R_4$ and $R_5$ are each independently represented by hydrogen or a $C_{1-4}$ alkyl, or —$OCH_2OR_3$ in which $R_3$ is as defined above, and a pharmaceutically acceptable basic addition salt thereof; in admixture with a pharmaceutically acceptable carrier.

29. A pharmaceutical composition according to claim 28 wherein X is represented by an ethylene.

30. A pharmaceutical composition according to claim 28 wherein $R_1$ and $R_2$ are represented by OH.

31. A pharmaceutical composition according to claim 29 wherein said R is a 4,6-dichloro-substituent.

32. A pharmaceutical composition according to claim 28 wherein said compound is 3-(2-Carboxy-6-methoxyindol-3yl)propionic acid.

33. A pharmaceutical composition according to claim 28 wherein said compound is 3-(2-Carboxy-6-chloroindol-3 yl)propionic acid.

34. A pharmaceutical composition according to claim 28 wherein said compound is 3-(2-Carboxy-4,6-dichloroindol-3-yl)propionic acid.

35. A pharmaceutical composition according to claim 28 wherein said compound is 3-(2-Carboxy-6-trifluoromethoxyindol-3-yl)propionic acid.

36. A pharmaceutical composition according to claim 28 wherein said compound is 3-(2-Carboxy-4-trifluoromethylindol-3-yl)propionic acid.

37. A pharmaceutical composition according to claim 28 wherein said compound is 3-(2-Carboxy-6-trifluoromethylindol-3-yl)propionic acid.

38. A pharmaceutical composition according to claim 28 wherein said compound is 3-(2-Carboxy-4-fluoroindol-3-yl)propionic acid.

39. A pharmaceutical composition according to claim 28 wherein said compound is 3-(2-Carboxy-4-nitroindol-3-yl)propionic acid.

40. A pharmaceutical composition according to claim 28 wherein said compound is 3-(2-Carboxy-6-nitroindol-3-yl)propionic acid.

41. A pharmaceutical composition according to claim 28 wherein said compound is ethyl 3-(2-carboxyethyl-4,6-dichloroindol-3-yl) propionate.

42. A pharmaceutical composition according to claim 28 wherein said compound is benzyl 3-(2-carboxybenzyl-4,6-dichloroindol-3-yl) propionate.

43. A pharmaceutical composition according to claim 28 wherein said compound is 3-(2-Carboxamide-4,6-dichloroindol-3-yl)propionamide.

44. A pharmaceutical composition according to claim 28 wherein said compound is 2-(2-Carboxy-6-chloroindol-3-yl)acetic acid.

45. A pharmaceutical composition according to claim 28 wherein said compound is 4-(2-Carboxy-6-chloroindol-3-yl)butyric acid.

46. A pharmaceutical composition according to claim 28 wherein said compound is 5-(2-Carboxy-6-chloroindol-3-yl)pentanoic acid.

47. A pharmaceutical composition according to claim 28 wherein said compound is 3-(2-Carboxy-4,6-dichloro-1-methylindol-3-yl).

* * * * *

UNITED STATES PATENT AND TRADEMARK OFFICE
CERTIFICATE OF CORRECTION

PATENT NO. : 4,960,786
DATED : October 2, 1990
INVENTOR(S) : Francesco G. Salituro et al.

It is certified that error appears in the above-identified patent and that said Letters Patent is hereby corrected as shown below:

```
   At column 8, line 14, the patent reads "-3yl)" and should
read -- -3-yl) --.

At column 8, line 17, the patent reads "-3 yl)" and should
read -- -3-yl) --.
```

Signed and Sealed this

First Day of June, 1993

Attest:

Attesting Officer

MICHAEL K. KIRK

Acting Commissioner of Patents and Trademarks